United States Patent [19]

Shizuya et al.

[11] Patent Number: 5,317,098
[45] Date of Patent: May 31, 1994

[54] NON-RADIOISOTOPE TAGGING OF FRAGMENTS

[76] Inventors: Hiroaki Shizuya, 1632 Indiana Ave., South Pasadena, Calif. 91030; Sharon L. Millar, 1825 Lanai St., West Covina, Calif. 91792

[21] Appl. No.: 840,090

[22] Filed: Mar. 17, 1986

[51] Int. Cl.$^5$ ................ C07H 21/02; C07H 21/04
[52] U.S. Cl. .................. 536/23.1; 536/24.30; 536/24.31; 536/24.32
[58] Field of Search ............ 536/27, 28, 29, 23.1, 536/24.31, 24.32, 24.30, 25.3; 435/6, 968; 935/77

[56] References Cited

FOREIGN PATENT DOCUMENTS

| 0169495 | 9/1985 | Japan | 536/28 |
| 8602929 | 5/1986 | PCT Int'l Appl. | 536/28 |
| 8606726 | 11/1986 | PCT Int'l Appl. | 536/29 |

Primary Examiner—Amelia Burgess Yarbrough
Attorney, Agent, or Firm—John E. Halamka

[57] ABSTRACT

A fragment, synthetic or natural, DNA or RNA, may be attached to a non-radiological label such as a fluorescent compound, a luminescent compound or a color reflective compound, by a linker. The linker is an aminoalkylphosphoramide. The linker may contain a number of methyl units selected to adjust the mobility of the arrangement of the tagged fragment in a polyacrylamide gel during electro-phoresis. A unique color may be attached to each for the four bases. The color coded bases may be separated in a single lane of the ployacrylamide gel. Because the mobility of each arrangement has been adjusted the normal one base spacing will be produced. The sequence of the target may be read directly by manually observing the color sequence or by an automatic reader. The tagging of natural fragments may be used to tag a preselected gene, in the application of Southern and Northern bloting diagnostic procedures, as a diagnostic tool to hunt/detect selected DNA and to label probes to detect ribosonal RNA of pathogens.

18 Claims, 2 Drawing Sheets

NON-RADIOISOTOPE TAGGING OF FRAGMENTS

BACKGROUND OF THE INVENTION

1. Field of the Invention

This invention relates to the genetic engineering and recombinant DNA art and, more particularly, to an improved tagging or labeling of fragments with fluorescent, luminescent, or color reflective labels.

2. Description of the Prior Art

The modern history of genetic engineering is generally accepted to have begun in 1973 when refinements in analytic methods uncovered unanticipated complexities and subtleties in the organization, replication, and expression of DNA. Revision of earlier concepts have been dependent upon the use of molecular tools for dissecting, cloning, and amplifying genomes.

The ability to sequence the DNA is one of the most fundamental and important technological advancements in basic research and now in clinical medicine. Most of the current methods of DNA sequence analysis utilize biologically hazardous, short lived radioisotopes such as phosphorus 32 (32P) to tag the DNA in vitro for determining the size and composition of fragments. However, the process of sequencing is labor intensive and time consuming.

In the chemical method of sequence analysis, the terminal nucleotide of a fragment is labeled and then hydrolyzed by base-specific reaction. The enzymatic replication method of sequence analysis incorporates the cloning of the gene that is to be sequenced and then attaching it to a single stranded DNA bacteriophage. A primer DNA which has the complementary base sequence to the DNA segment adjacent to the cloned gene is used to initiate the copying of the cloned DNA. The process of this synthesis requires four kinds of deoxyribonucleoside triphosphates (dATP, dCTP, dGTP and dTTP) as precursers and four different dideoxyribonucleoside triphosphates (ddATP, ddCTP, ddGTP and ddTTP) as chain terminators. Reaction mixtures for copying the DNA containing all four precursers and only one each of the four chain terminators are placed in four separate tubes. When a dideoxytriphosphate is incorporated to the copied DNA, the subsequent DNA synthesis ceases immediately and chain termination occurs. As a result, all the copied DNA with ddATP, for example, terminates at positions where dATP is normally incorporated. Since incorporations of dideoxytriphosphates occur anywhere in the copied DNA, various lengths of DNA, with dideoxytriphosphate bases at their termini are generated. The copied DNA fragments are then separated by polyacrylamide gel electro-phoresis according to the number of bases in each fragment of DNA. In order to detect the DNA on the gel, a radioactive tag such as 32P labeled deoxyribonucleoside triphosphate is incorporated into the copied DNA. The radioactive DNA is separated on the gel and visualized by exposing the gel to x-ray film. The sequence of the copied DNA is read from the autoradiograph of the gel.

Others have attempted to substitute elements such as fluorescent or luminescent tagging for radioactive tagging. A method developed by Smith, Fung and others The synthesis of oligonucleotides containing an aliphatic amino group at the 5' terminus: synthesis of fluorescent DNA primers for use in DNA sequence analysis, *Nucleic Acids Research*, Volume 13, Number 7, 1985, page 2399. utilizes chemically synthesized DNA primers with a covalently attached fluorophores as a substitute for the radiolabeled nucleoside triphosphate for use in DNA sequence analysis. However, each fluorescent compound utilized must fluoresce at a significantly different wave length from the other three compounds in order for the user to observe the compound separate and apart from the others. Therefore, four different compounds must be used. The chemical characteristics of each compound is sufficiently different to alter the mobility of the primers in a polyacrylamide gel electrophoresis. This alteration is readily apparent when attempting to read the pattern of bands after separation. The normal separation of fragments by one base pair in each lane of the gel is compromised by this delta-difference in chemical characteristics of the fluorescent compounds by displacing the band by more than the normal band width for a base pair. Thus the accuracy of determination of the DNA sequence is compromised.

Thus, there has long been a need for a non-radiological tagging which could incorporate compensation for the chemical characteristics of the tagging.

Further, it is also desired that the tagging utilize only a single lane in polyacrylamide gel electro-phoresis in order to allow simplified automatic analysis of sequencing.

Further, it is also desired that the tagging be useful on natural as well as synthesized DNA primers.

SUMMARY OF THE INVENTION

Accordingly, it is an object of the present invention to provide a non-radiological tagging of nucleosides, oligonucleotides and nucleic acids (synthetic or natural) with fluorescent, luminescent or color reflective molecules.

It is another object of the present invention to provide a capability of adjusting the increment of polyacrylamide gel electro-phoresis mobility of the tagged oligonucleotides and nucleic acids.

It is yet another object of the present invention to provide a tagging which assigns a unique preselected fluorescent bandwidth to each of the four bases and can compensate for the chemical characteristics of each fluorescent compound. Thus, a single lane in a gel can separate the fragments and each base unit can be readily identified by the unique fluorescent color.

It is yet another object of the present invention to provide a tagging of natural as well as synthetic DNAs.

It is a further object of the present invention to provide non-radioactive labeling nucleic acid to provide a diagnostic tools such as a probe to detect human DNA or RNA and to detect and identify pathogen bacteria.

The above and other objects of the present invention are achieved, according to a preferred embodiment thereof, by providing a method for tagging oligonucleotides nucleosides, and nucleic acids with various fluorescent, luminescent or color reflective molecules.

BRIEF DESCRIPTION OF THE DRAWING

The above and other embodiments of the present invention may be more fully understood from the following detailed description, taken together with the accompanying drawing, wherein similar reference characters refer to similar elements throughout, and in which.

DESCRIPTION OF A PREFERRED EMBODIMENT

Figure 1:
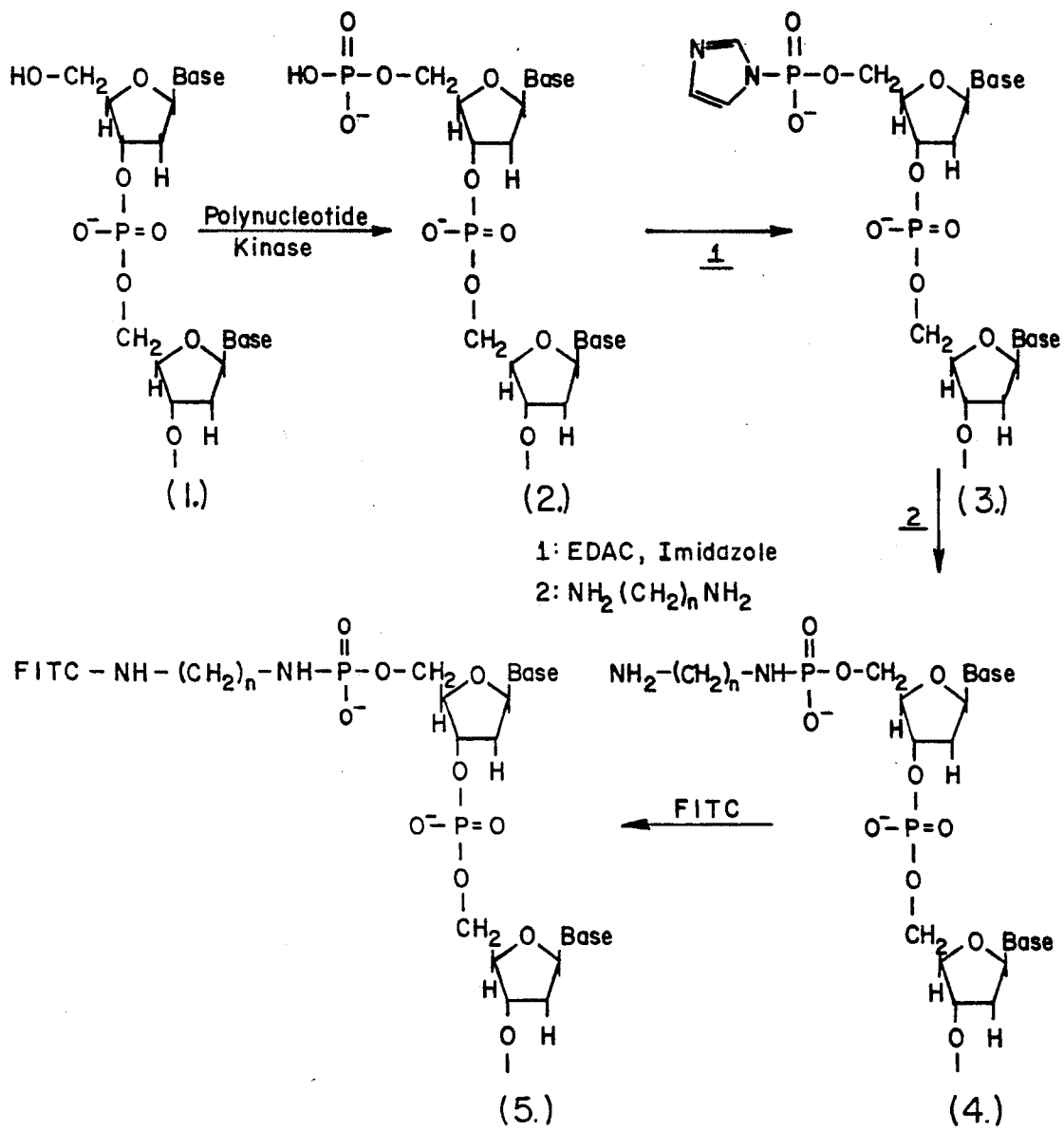
FIG. 1 is the process used to create the labeled, labeled in this case with the fluorescent compound FITC.

Referring now to the drawing, there is illustrated in FIG. 1 a fragment consisting in this case of a single stranded oligonucleotide generally depicted in schematic form, having a plurality of bases and a 5'end. The biological fragment may be a single base, may be DNA or RNA and may be synthetic or natural.

The preferred length of the oligonucleotide segment is at least fifteen bases. The oligonucleotide can be natural or synthesized using the solid-phase CED-phosphoramidite method on an automated DNA synthesizer such as a Systec model 1540A.

Phosphorylation of the 15 mers synthesized oligonucleotide was performed in a final volume of 100 ul containing 50 mM Tris-CHl pH 7.6, 10 mM MgCl2, 10 mM dithiothreitol, 3 mM ATP and T4 polynucleotide kinase at 37° C. for 1 hr. The phosphorylated oligonucleotide was purified by HPLC using a gel filtration column (SW 2000 Toyo Soda). The oligonucleotide peak was collected and dried under vacuum. Ammonium acetate was removed by repeated lyophilization with H2O.

The linker between the 5' end of the oligonucleotide and the fluorescent compound is aminoalkylphosphoramide with various lengths of polyhydrocarbons. This compound consists of an amino (NH2) at each end and a plurality of methyl units (CH2)n between. The number of methyl units is preselected to compensate for the difference in chemical characteristics of the fluorescent, luminescent, or color reflective compounds attached to the selected oligonucleotides. Experimental evidence shows that four methyl units will decrease the mobility of an oligonucleotide by the distance of one base. Therefore, the mobility of the tagged oligonucleotides may be adjusted to the accuracy of $\frac{1}{4}$ of the normal spacing between lines obtained during electro-phoresis in a lane of a polyacrylamide gel. The linker compound, NH2(CH2)nNH2 (diaminoalkane), is commercially available for a range of n from 2 to 12 which is sufficient to adjust the weight of most combinations of fluorescent compounds, luminescent compounds and color reflective (light absorbing) compounds. Examples of different alkanes are: 1,2 diaminoethane (n=2), 1,6 diaminohexane (n=6) and 1,10 diaminodecane (n=10).

To attach the linker, chosen in this example to have n equal to 2 and depicted in FIG. 1 as NH2(CH2)2NH2, the oligonucleotide was incubated in a final volume of 100 ul containing 250 mM 1,2 diaminoethane pH 6.0, 200 mM ethyl-3 (3-dimethyl-amino-propyl) carbodiimide (EDAC) and 100 mM N-methylimidazole pH 6.0 at 25 C. overnight.

To tag the oligonucleotide and linker with the fluorescent compound, shown in FIG. 1 to be fluorescein isothiocyanate (FITC), the amino alkyl phosphoramidate DNA was dissolved in 50 ul of 0.2M NaCO3 buffer pH 9.3 containing 15 ul of 2 mg/ml FITC dissolved in dimethylformamide (DMF) and incubated at 25 C. overnight in the dark. The FITC labeled DNA is purified by HPLC as described above.

The final product is a primer connected by a linker to a fluorescent compound.

Sequencing may now proceed using the method described by F. Sanger with the single color tag taking the place of a radioisotope tag. The sequencing method requires four lanes in a polyacrylamide gel, one for each type of base.

A polyacrylamide gel can produce a "smile" effect. The mobility of the oligonucleotides in the outside lanes can be slower and produce an ambiguity in spacing. Normally the lines in the lanes are spaced at least one unit apart corresponding to the difference in weight of one nucleotide. The "smile" effect may make it difficult to unambiguously determine the next nucleotide in sequence.

The ideal procedure would make use of only one lane. This would eliminate the smile effect. However, the observer must be able to detect a difference between a line for an oligonucleotide terminating in thymine or uracil from a line terminating in cytosine, adenine or guanine. It is possible to use a tag of a specific fluorescent wavelength for each of the four types of bases. The preparation of the oligonucleotides uses a preselected compound having a selected wavelength to be associated with only one base. This has been done in the prior art "Fluorescence detection in automated DNA sequence analysis," Smith, Sanders, and others, Nature, Vol. 321, Jun. 12, 1986, p. 674. however the results produced are ambiguous. This prior art technique joins a fluorescent compound to the aminated 5' end of a synthetic oligonucleotide. Making protected amino-derivatized nucleotide phosphoramidites is laborious and requires technical expertise. Further, only synthetic oligonucleotides can be labeled by this technique. Finally, the mobility of the tagged oligonucleotides cannot be adjusted.

Each fluorescent compound used as a tag has unique chemical characteristics that change the mobility of the tagged oligonucleotide. The factors effecting mobility include for example: ionization, molecular weight of the tagging compound, and the shape of the molecule of the tagging compound. The change in mobility can be so pronounced as to be easily visualized by the location of a line that is not at the normal spacing of one base. If the change in mobility of each of the four tagged oligonucleotides should result in two or more of the lane spacing being shifted by plus and minus amounts nearly totaling the normal spacing, the user may not be able determine which base in next in the lanes of the gel. In particular, if the four lanes were combined into a single lane for optical reading by a machine for automatic sequencing, the unequal spacing would render the readings ambiguous.

This invention allows the attachment of a fluorescent, luminescent, or color reflective tag with a linker which has a preselected plurality of methyl units, n. The preselected number (n) of methyl units in the linker is used to adjust the mobility of each tagged oligonucleotide to obtain the normal one base spacing between lines in the lane of the gel.

The choice of n is determined by the number and type of tags used in the final process.

For example, if four different fluorescent tags are to be used, one for each of the four different bases, the chemical characteristics of the fluorescent compounds can be significantly different. After the fluorescent tags are attached to the primer, the mobility of each primer is different for each of the four different compounds. In the prior art, the radioisotope was the same for all primers. Thus, the mobility was equally changed for each base. The mobility of the tagged primers can be adjusted by changing the number of methyl units in the linker for that fluorescent compound. In order to adjust the mobility of each tagged primer so that the mobility is the same, additional weight is first added to those primers having a fluorescent tag having molecular weight less than the maximum. The extra weight being in the form of N methylene groups contained in the linker between the 5' end of the oligonucleotide and the fluorescent compound. The number of methylene groups is determined by computing the molecular weight of each fluorescent compound. The fluorescent compound with the most weight will be attached to the primer by a linker having an N of 2. An estimate of the additional weight to be added to each of the lesser weight fluorescent compounds can be achieved by subtracting the weight of the lesser weight fluorescent compounds from the compound with the maximum weight. The difference is used to compute the number of methylene (CH$_2$) units required in the linker. Four separately tagged primers with the weight adjustment should be prepared and run in four lanes of a gel. If other chemical characteristics of the fluorescent compound affect mobility, the position of the tagged primers in the gel will show a misalignment. Each added methyl unit will retard the mobility of the tagged primer by approximately ¼ of the normal spacing. After each trial and subsequent adjustment, another four lanes, each containing a primer tagged with a different color fluorescent compound should be run until each lane aligns with the remaining lanes. The tagged and mobility adjusted primers are now ready to be used in a selected sequencing scheme.

The same process of adjustment of mobility can be used for luminescent, or color reflective labels e.g. photobiotin, barite, etc.

The four fluorescent compounds selected for this invention are:

Fluorescein isothiocyanate (FITC) with maximum emission peak at 515 nm (green color);

4-Fluoro-7-nitrobenzo-furazan (NBD-F) at 540 nm (yellowish green);

Tetramethylrhodamine isothiocyanate (TRITC) at 573 nm (orange color); and,

Tetramethyl isothiocyanate (XRITC) at 601 nm (red color).

Figure 2:
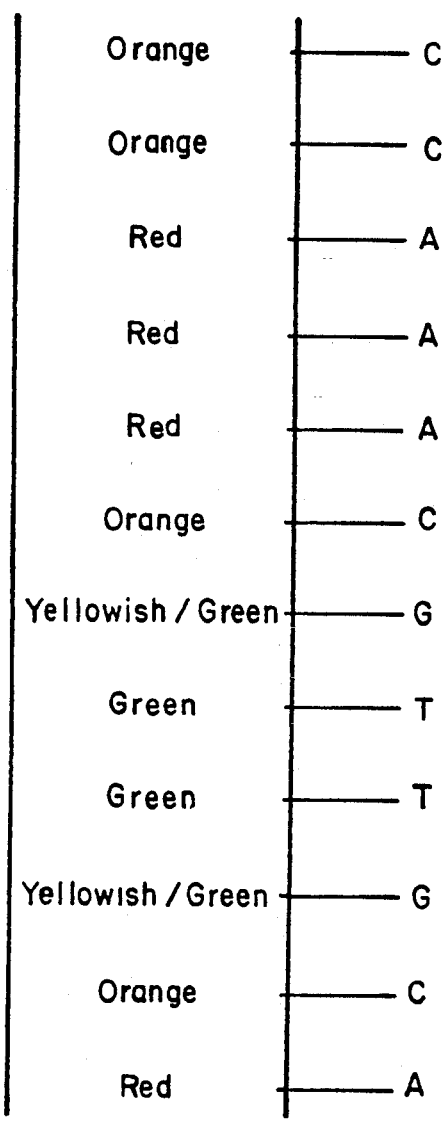
FIG. 2 is a polyacrylamide gel with one lane.

Each of the four fluorescent labels is attached to the DNA primer via a linker. For DNA synthesis, four reaction mixtures are used and each contains one kind of fluorescent labeled primer (e.g., XRITC) and a dideoxynucleotide (e.g. ddATP) Thus, after the DNA is synthesized, all the copied DNA molecules terminating with ddA are labeled with the red colored XRITC, ddC terminated DNA with the orange colored TRITC, ddG terminated DNA with the yellowish green colored DBD-F and ddT terminated DNA with the green colored FITC. Unlike the radioactive label method which uses four lanes in the polyacrylamide gel electro-phoresis, this new method uses only one lane. All four fluorescent reaction mixtures are combined in one tube and applied to the gel electro-phoresis. Fluorescent labeled DNAs are then separated by size, and individual bands are seen on the gel. A laser or visible light source may be used to scan the gel and to excite the fluorescent labels for emission of characteristic color according to the label. FIG. 2 demonstrates how the single lane on the gel, with the above associaton of color to base, may be used to directly read the sequence.

The emission from each band may readily be detected by photography. The emission from each band may be detected by a photo sensitive detector in an automatic sequencing machine.

The ease of tagging natural as well as synthetic fragments allows general tagging to be used for general tagging of a preselected gene. As shown in the references to the prior art, only synthetic biological fragments could be tagged. With the process disclosed in the present invention, natural biological fragments can be tagged with nonradioisotope markers.

Further, the tagging may be applied to Southern and Northern bloting diagnostic procedures.

The tagging lends itself to be used as a diagnostic tool to label a probe to hunt/detect selected DNA.

Pathogens can be detected using labeled probes to detect ribosonal RNA.

This concludes the description of a preferred embodiment of the present invention. Those skilled in the art may find many variations and adaptions falling within the scope of this invention, and the appended claims are intended to cover all such variations and adaptions falling within the true scope and spirit of the invention.

What is claimed is:

1. Labeled RNA and DNA fragment in which a segment portion thereof, having a 5'-phosphate end, has the formula

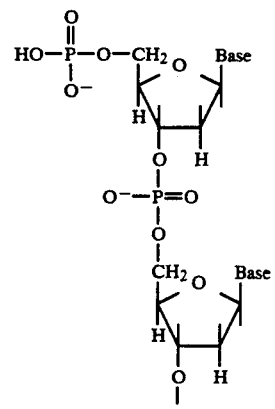

a linker portion thereof has the formula, NH$_2$(CH$_2$)$_n$NH$_2$, terminating in an amino at the first end and an amino at the second end, a plurality, n, of methylene units in a chain between said ends, and said first end bonded to said 5'-phosphate end of said segment, said plurality, n, of methylene units is preselected for the chemical characteristics of the fluorescent compound such that the summation of the chemical characteristics of said linker portion plus said chemical characteristics of said fluorescent compound may be adjusted by the selection of n to produce a preselected mobility of said arrangement in a polyacrylamide gel, whereby the spacing of adjacent bands in electro-phoresis separation is controlled; and, a fluorescent compound bonded to said second end.

2. The arrangement defined in claim 1 wherein:
said fluorescent compound is preselected to fluoresce at a perceptibly different wavelength from a plurality of fluorescent compounds whereby a particular fluorescent band is discernible from other fluorescent bands in a polyacrylamide gel electro-phoresis separation.

3. The arrangement defined in claim 1 wherein:
said segment is natural DNA.

4. The arrangement defined in claim 1 wherein:

said segment is synthetic DNA.
5. The arrangement defined in claim 1 wherein: said segment is natural RNA.
6. The arrangement defined in claim 1 wherein: said segment is synthetic RNA.
7. Labeled RNA and DNA fragment in which a segment portion thereof, having a 5'-phosphate end, has the formula

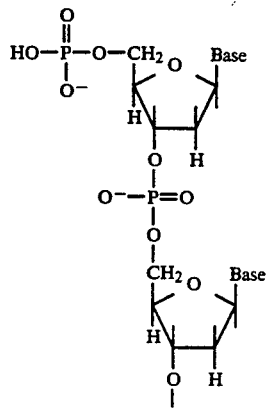

a linker portion thereof has the formula, $NH_2(CH_2)_nNH_2$, terminating in an amino at the first end and an amino at the second end, a plurality, n, of methylene units in a chain between said ends, and said first end bonded to said 5'-phosphate end of said segment, said plurality, n, of methylene units is preselected for the chemical characteristics of the luminescent compound such that the summation of the chemical characteristics of said linker portion plus said chemical characteristics of said luminescent compound may be adjusted by the selection of n to produce a preselected mobility of said arrangement in a polyacrylamide gel, whereby the spacing of adjacent bands in electro-phoresis, separation is controlled; and, a luminescent compound bonded to said second end.

8. The arrangement defined in claim 7 wherein: said luminescent compound is preselected to have a characteristic luminescence at a perceptibly different wavelength from a plurality of luminescent compounds whereby a particular luminescent band is discernible from other luminescent bands in a polyacrylamide gel electro-phoresis separation.

9. The arrangement defined in claim 7 wherein: said segment is natural DNA.

10. The arrangement defined in claim 7 wherein: said segment is synthetic DNA.

11. The arrangement defined in claim 7 wherein: said segment is natural RNA.

12. The arrangement defined in claim 7 wherein: said segment is synthetic RNA.

13. Labeled RNA and DNA fragment in which a segment portion thereof, having a 5'-phosphate end, has the formula

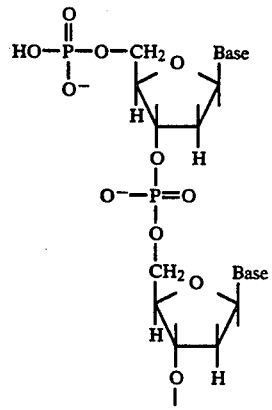

a linker portion thereof has the formula, $NH_2(CH_2)_nNH_2$, terminating in an amino at the first end and an amino at the second end, a plurality, n, of methylene units in a chain between said ends, and said first end bonded to said 5'-phosphate end of said segment, said plurality, n, of methylene units is preselected for the chemical characteristics of said color reflective compound such that the summation of the chemical characteristics of said linker portion plus said chemical characteristics of said reflective compound may be adjusted by the selection of n to produce a preselected mobility of said arrangement in a polyacrylamide gel, whereby the spacing of adjacent bands in electro-phoresis separation is controlled; and a color reflective compound bonded to said second end.

14. The arrangement defined in claim 13 wherein: said color reflective compound is preselected to reflect a color of a perceptibly different wavelength from a plurality of color reflective compounds whereby a particular color reflective band is discernible from other color reflective bands in a polyacrylamide gel electro-phoresis separation.

15. The arrangement defined in claim 13 wherein: said segment is natural DNA.

16. The arrangement defined in claim 13 wherein: said segment is synthetic DNA.

17. The arrangement defined in claim 13 wherein: said segment is natural RNA.

18. The arrangement defined in claim 13 wherein: said segment is synthetic RNA.

* * * * *